United States Patent [19]

Kerwin et al.

[11] Patent Number: 4,687,744

[45] Date of Patent: Aug. 18, 1987

[54] ARTIFICIAL CULTURE OF THE SEXUAL STAGE OF LAGENIDIUM GIGANTEUM

[75] Inventors: James L. Kerwin, Woodland; Robert K. Washino, Davis, both of Calif.

[73] Assignee: The Regents of the University of California, Berkeley, Calif.

[21] Appl. No.: 622,094

[22] Filed: Jun. 19, 1984

Related U.S. Application Data

[63] Continuation-in-part of Ser. No. 431,176, Sep. 30, 1982, abandoned.

[51] Int. Cl.$^4$ .......................... C12N 3/00; C12N 1/38; C12N 1/14; C12R 1/645
[52] U.S. Cl. .................................... 435/242; 435/244; 435/254; 435/911
[58] Field of Search .............. 435/242, 243, 244, 254, 435/260, 820, 911; 424/93

[56] References Cited

U.S. PATENT DOCUMENTS

| | | | |
|---|---|---|---|
| 3,183,171 | 5/1965 | Schreiner | 435/254 |
| 3,293,145 | 12/1966 | Leavitt et al. | 435/244 |
| 3,508,927 | 4/1970 | Herndon et al. | 435/244 |
| 4,166,006 | 8/1979 | Hertl et al. | 435/244 |
| 4,530,834 | 7/1985 | McCabe et al. | 424/93 |

OTHER PUBLICATIONS

Brey, Paul T.; "Observations of In Vitro Gametangial Copulation and Oosporogenesis in *Lagenidium giganteum*", *J. Invt. Path.*, 45 (1985), pp. 276–281.

Domnas et al.; "Sterol Requirement for Zoospore Formation in the Mosquito—Parasitizing Fungus *Langenidium giganteum*"; *Mycologia*, 69 (1977), pp. 875–886.

Domnas et al.; "Biochemistry of Mosquito Infection . . . with *Lagenidium giganteum*", *J. Invt. Path.*, 24 (1974), pp. 293–304.

Hawley, ed. *The Condensed Chemical Dictionary*, 10th ed., (1981), Van Nostrand Reinhold Co., N.Y., p. 522.
Windholz ed.; *The Merck Index*, Merk & Co., Inc., Rahway, N.J., 10th ed. (1983), p. 1249.

*Primary Examiner*—Thomas G. Wiseman
*Assistant Examiner*—Elizabeth C. Weimar
*Attorney, Agent, or Firm*—Flehr, Hohbach, Test, Albritton & Herbert

[57] ABSTRACT

A method is provided for producing oospores of the organism *Lagenidium giganteum* comprising the steps of incubating zoospores with a medium containing a sterol and particular fatty acids or fatty acid derivatives.

4 Claims, No Drawings

ARTIFICIAL CULTURE OF THE SEXUAL STAGE OF LAGENIDIUM GIGANTEUM

This invention was made with Government support under subcontract L800200 RF, Project 4148, under Contract OMB 81-2235 USC 200-206 awarded by the Environmental Protection Agency. The Government has certain rights in this invention.

This is a continuation-in-part of Ser. No. 431,176, filed Sept. 30, 1982, now abandoned.

The present invention is directed to a method for producing the sexual stage of the organism Lagendium giganteum. In particular, the present invention is directed to a method of producing oospores in vitro by incubating zoospores or hyphal segments of *L. giganteum* in a medium containing a particular unsaturated fatty acid, unsaturated fatty acid glyceride or unsaturated fatty acid polyglyceride.

The fungus *Lagenidium giganteum* is a facultative endoparasite of anopheline and culicine mosquito larvae. The zoospores of *L. giganteum* actively seek out mosquito hosts and the fungus persists in an active state as long as susceptible hosts are present. If the water source in which the mosquito larvae live dries out, the fungus remains in a dormant state in the form of oospores. Therefore it is desirable to be able to artificially cultivate the oospores of *L. giganteum* on large scale in order to utilize it as a biological insecticide for mosquito larvae.

The only currently registered biological insecticide for mosquito larvae is the bacterium *Bacillus thuringiensis israelensis* (BTI). The disadvantage of BTI is that it persists for a maximum of about 48 hours following application under field conditions and it must be ingested by the mosquito larvae.

It is therefore an object of the present invention to provide a method for producing oospores of *L. giganteum* in vitro whereby oosporogenesis is artificially induced by exogenous components.

The fungus *L. giganteum* may undergo either an asexual or sexual reproductive cycle. In the asexual cycle motile zoospores of *L. giganteum* selectively encyst on the cuticle of mosquito larvae, which is pierced enzymatically and mechanically by the fungus. The fungal mycelium subsequently ramifies throughout the larvae until the larval body cavity is completely filled with septate hyphae of the fungus. Hypha segments can develop into zoosporangia and zoospores may be discharged through an exit tube into the environment, thereby continuing the asexual infection cycle. Alternatively, adjacent hyphal segments of the fungus can develop into antheridia (male organs in male sexual cells) and oogonia (female sexual organs in female sexual cells). Subsequent fusion of the protoplasts and nuclei of adjacent hyphal segments by plasmogamy and karyogamy results in thick-walled oospores. The oospores may remain dormant until the correct environmental conditions induce germination, resulting in motile zoospores to initiate the infection cycle.

The present invention is directed to a method for producing oospores of the organism *L. giganteum* comprising the step of inducing oospore formation by contacting the zoospores with a medium containing a particular unsaturated fatty acid or unsaturated fatty acid derivative, or mixture thereof.

The process for artificial culturing according to the present invention may be conducted on agar media or in liquid culture utilizing rotary shakers or industrial scale fermentation technology. Generally, the process according to the present invention involves growing L giganteum in a growth medium, inducing zoosporogenesis and introducing the resultant zoospores to a nutrient medium to induce oosporogenesis.

According to the present invention, cultures of *L. giganteum* may be maintained on a modified peptone yeast extract-glucose (PYG) agar medium as disclosed by Brown et al. *Amer. J. Bot. J.*, 42:337-341 (1955), supplemented with 1.5% (w/v) Mazola ® corn oil. This commercial corn oil contains a mixture of sterols including stigmasterol, beta-sitosterol, and gamma-sitosterol or campesterol, and C-16 and C-18 saturated and unsaturated fatty acids. Alternatively, the organism may be maintained on an agar medium of the following composition: 1.25 g D-glucose, 1.25 g Difco peptone, 1.25 g Ardamine pH (autolyzed yeast extract, Desmo Chemical Corporation, Elmsford, NY), 2.0 g corn oil, 1.0 g Grumbacher ® linseed oil, 0.075 g $CaCl_2.2H_2O$ and 20 g Difco agar per liter of deionized water.

Zoosporogenesis may be induced by placing a small amount of surface mycelium of hyphal segments from 7- to 14-day old cultures of *L. giganteum* into sterile deionized water in a 10-cm-diam petri dish. Sufficient densities of zoospores ($1.5-2.0 \times 10^4$/ml) are available for further transfer into the oospore-inducing medium within 12 to 18 hours.

To induce oospore production 8 ml of zoospore suspension ($1.2-1.6 \times 10^5$ zoospores) may be inoculated into each 100 ml of oospore-inducing media. Cultures may be incubated for six days on a rotary shaker at $110 \pm 5$ rpm under ambient conditions of temperature ($22° \pm 5°$ C.) and light. Quantitative oospore yields may be obtained using a hemocytometer beginning a minimum of 10 days post-inoculation. Oospore viability may be determined visually. Cultures may be homogenized, for instance, at high speed for ca. 30 seconds in an Osterizer blender prior to counting.

The oospore-inducing medium according to the present invention comprises an assimilable source of carbon, such as glucose, sucrose, and the like; an assimilable source of nitrogen; a sterol; a non-toxic calcium or magnesium salt; and an unsaturated fatty acid or derivative selected from the group consisting of oleic acid, palmitoleic acid, oleic acid esters, palmitoleic acid esters, linoleic acid esters, diolein, triolein, trilinolein and mixtures thereof. The sterol may be cholesterol or a cholesterol-like sterol, such as, 7-dehydrocholesterol, sitosterol, desmosterol, fucosterol, stigmasterol, cholesteryl acetate, cholesteryl palmitate, and the like. Cholesterol is preferred. The non-toxic salts are preferably the chlorides of calcium or magnesium. The medium may also contain other convention components, such as buffers. A preferred group of fatty acid or derivative compounds comprises palmitoleic acid, diolein, triolein, trilinolein or mixtures thereof.

The following Table 1 illustrates the effect of cholesterol, cholesteryl esters, fatty acids and fatty acid derivatives on in vitro oosporogenesis of *L. giganteum*.

TABLE 1
EFFECT OF CHOLESTEROL ESTERIFICATION AND CHOLESTEROL AND FATTY ACID CONCENTATION ON OOSPOROGENESIS

| Sterol/Concn. (mg/L)[1] | Fatty Acid/ Concn. (g/L) | Oospore Yield $(\times 10^{-6})^2$ % Viability |
|---|---|---|
| Sterols and Sterols Esters | | |
| Cholesterol/5 | — | 0 |
| Cholesterol/10 | — | 0.05/0 |
| Cholesterol/50 | — | 0.40/0 |
| Cholesterol/100 | — | 0.23/0 |
| Cholesteryl Oleate/10 | — | 0.23/0 |
| Cholesteryl Oleate/25 | — | 0.18/0 |
| Cholesteryl Oleate/50 | — | 0.03/0 |
| Cholesteryl Oleate/100 | — | 0.05/0 |
| Cholesteryl Linoleate/10 | — | 0.15/0 |
| Cholesteryl Linoleate/25 | — | 0.61/0 |
| Cholesteryl Linoleate/50 | — | 0/0 |
| Cholesteryl Linoleate/100 | — | 0.05/0 |
| Sterols and Unsaturated Fatty Acids | | |
| Cholesterol/25 | Myristic/1.0 | 0.15/48 |
| " | Trimyristion/1.0 | 0.40/50 |
| " | Palmitic/1.0 | 0.10/25 |
| " | Tripalmitin/1.0 | 0.87/16 |
| " | Stearic/1.0 | 0.46/24 |
| Cholesterol 25 | Tristearin/1.0 | 0.12/17 |
| " | Arachidic/1.0 | 0.13/0 |
| " | Palmitoleic/0.25 | 6.1/6 |
| " | Palmitoleic/0.5 | 5.7/72 |
| " | Tripalmitolein/0.25 | 4.2/48 |
| " | Oleic/0.1 | 0.32/5 |
| " | Oleic/1.0 | 1.0/30 |
| " | Monoolein/0.25 | 0.5/0 |
| " | Monoolein/0.5 | 0.83/0 |
| " | Monoolein/1.0 | 3.2/8 |
| " | Diolein/0.25 | 2.1/16 |
| " | Diolein/0.5 | 2.9/62 |
| " | Triolein/0.1 | 3.6/8 |
| " | Triolein/0.25 | 3.1/23 |
| " | Triolein/0.5 | 4.2/72 |
| " | Linoleic/0.1 | 0.33/15 |
| " | Linoleic/0.25 | 0/0 |
| " | Linoleic/1.0 | TOXIC |
| " | Monolinolein/0.25 | 0.49/0 |
| " | Monolinolein/1.0 | 1.7/0 |
| " | Dilinolein/0.25 | 0.38/22 |
| " | Dilinolein/1.0 | 1.8/39 |
| " | Trilinolein/0.1 | 3.8/0 |
| " | Trilinolein/0.25 | 4.5/37 |
| " | Trilinolein/0.5 | 6.2/78 |
| Cholesterol 25 | Trillinolein/0.1 | 4.7/72 |
| " | Linolenic/1.0 | TOXIC |
| " | Trilinolenin/0.1 | 0 |
| " | Trilinolenin/0.25 | 0.15/11 |
| " | Trilinolenin/0.5 | 0.90/3 |
| " | Trilinolenin/1.0 | 0.90/0 |
| " | 11,14,17-Eicosatrienoic/0.25 | 0/0 |
| Sterols, Saturated and Unsaturated Fatty Acids | | |
| Cholesterol 25 | Triolein/0.25 Tripalmitin/0.1 | 0.43/0 |
| " | Triolein/0.25 Stearic/0.1 | 0.33/0 0.33/0 |
| " | Triolein/0.25 Tristearin/0.1 | 0.62/27 |
| Sterol Esterrs, Sterols and Unsaturated Fatty Acid | | |
| Cholesteryl Palmitate/25 | Triolein OR Trilinolein/0.25 | 0/0 |
| Cholesteryl Stearate/25 | Triolein OR Trilinolein/0.25 | 0/0 |
| Cholesteryl Oleate/25 | Triolein/0.25 | 2.1/67 |
| Cholesteryl Linoleate/25 | Triolein/0.25 | 0.92/60 |
| Cholesterol/12.5 Cholesteryl Palmitate/12.5 | Trilinolein/0.25 | 0.30/22 |
| Cholesterol/20 Cholesteryl Stearate/5 | Trilinolein/0.25 | 1.9/73 |
| Cholesterol/12.5 | Trilinolein/0.25 | 0.52/69 |

TABLE 1-continued

EFFECT OF CHOLESTEROL ESTERIFICATION AND CHOLESTEROL AND FATTY ACID CONCENTATION ON OOSPOROGENESIS

| Sterol/Concn. (mg/L)[1] | Fatty Acid/ Concn. (g/L) | Oospore Yield $(\times 10^{-6})$[2] % Viability |
|---|---|---|
| Cholesterol Stearate/12.5 | | |

[1]Added to basal medium of (g/L deionized water): 1.5 Ardamine pH, 0.5 Glucose, 0.05 Lecitin, 0.025 Cholesterol, 5 mM $CA^{2+}$.
[2]Oospore yield per 108 ml of medium.

The following Table 2 illustrates the effect of cations on in vitro oosporogenesis of L. giganteum.

TABLE 2

EFFECT OF CATIONS ON OOSPOROGENESIS

| Added Cation | Concentration (mM) | Oospore Yield $(\times 10^{-6})$[2]/ % Viability |
|---|---|---|
| None, 2 mM EGTA[3] | 0 | 0/0 |
| $Ca^{2+}$ | 5 | 4.6/68 |
| $Ca^{2+}$ | 10 | 2.1/85 |
| $Ca^{2+}$ | 20 | 1.3/86 |
| $Ca^{2+}$ | 30 | 5.6/17 |
| $Mg^{2+}$ | 1 | 2.2/52 |
| $Mg^{2+}$ | 5 | 4.9/53 |
| $Mg